United States Patent [19]

Schwarz et al.

[11] 4,340,744
[45] Jul. 20, 1982

[54] PREPARATION OF IMIDAZOLES

[75] Inventors: Helmut Schwarz, Ludwigshafen; Toni Dockner, Meckenheim; Uwe Kempe, Limburgerhof; Herbert Krug; Werner Praetorius, both of Ludwigshafen; Peter Magnussen, Bad Duerkheim; Ewald Gallei, Viernheim; Erich Fehr, Ludwigshafen, all of Fed. Rep. of Germany

[73] Assignee: BASF Aktiengesellschaft, Ludwigshafen, Fed. Rep. of Germany

[21] Appl. No.: 242,012

[22] Filed: Mar. 9, 1981

[30] Foreign Application Priority Data

Mar. 13, 1980 [DE] Fed. Rep. of Germany ....... 3009631

[51] Int. Cl.$^3$ .......................................... C07D 231/12
[52] U.S. Cl. .................................... 548/346; 548/335
[58] Field of Search ............... 548/335, 347, 355, 346

[56] References Cited

U.S. PATENT DOCUMENTS 2,847,417  8/1958  Erner .................................. 548/335

FOREIGN PATENT DOCUMENTS

| 1231249 | 12/1966 | Fed. Rep. of Germany . |
| 1952991 | 5/1970 | Fed. Rep. of Germany . |
| 2728976 | 1/1979 | Fed. Rep. of Germany . |
| 2729017 | 1/1979 | Fed. Rep. of Germany . |
| 2733466 | 2/1979 | Fed. Rep. of Germany . |
| 1266702 | 8/1964 | France . |
| 201418 | 8/1965 | U.S.S.R. . |

Primary Examiner—Henry R. Jiles
Assistant Examiner—Bernard Dentz
Attorney, Agent, or Firm—John H. Shurtleff

[57] ABSTRACT

Imidazoles are prepared by reacting 2-imidazolines at from 250° to 500° C. in the presence of molybdenum oxide and nickel oxide and/or cobalt oxide and aluminum oxide, silicon dioxide and/or silicates as catalysts.

The imidazoles obtainable by the process according to the invention are valuable starting materials for the preparation of dyes, crop protection agents, textile auxiliaries, catalysts for polyurethanes and epoxy resins, surfactants and drugs, for example the corresponding nitroimidazoles.

12 Claims, No Drawings

PREPARATION OF IMIDAZOLES

The present invention relates to a novel process for the preparation of imidazoles by reacting 2-imidazolines at from 250° to 500° C. in the presence of molybdenum oxide and nickel oxide and/or cobalt oxide and aluminum oxide, silicon dioxide and/or silicates as catalysts.

German Laid-Open Application DOS No. 1,952,991 discloses that alkylenediamines can be reacted with carbonyl compounds in the presence of a copper and/or chromium catalyst at 320°–650° C., to give imidazoles. As all the Examples show, hydrogen must additionally be fed to the reaction mixture; re-utilizable by-products are not obtained.

U.S. Pat. No. 2,847,417 describes the preparation of imidazoles from alkylenediamines and carboxylic acids over supported platinum metal catalysts. Such catalysts are expensive and are easily poisoned by certain materials, such as sulfur, heavy metals or halides. Noble metal catalysts have to be produced by expensive methods, to ensure uniform activity of the catalyst, and from very pure starting materials, so as not to diminish the activity of the catalyst. As is shown by the description (column 1, lines 50 to 70 and column 2, lines 65 to 70) and the Examples of the U.S. patent hydrogen is again added, in the process described, to avoid the formation of tarry polymers and deposits on the catalyst and so as to preserve the activity of the catalyst for as long as possible.

Russian Pat. No. 201,418 discloses that 2-methylimidazoline may be dehydrogenated to 2-methylimidazole over a metal catalyst, in diphenyl oxide as the reaction medium, at from 180° to 230° C. An Example in this patent describes a reaction employing 47 grams of starting material. If the reaction is carried out in the liquid phase on an industrial scale, the yield is much lower and can be less than 60% of theory. A substantial proportion of imidazole is formed by dealkylation, the proportion being the higher, the greater the conversion to 2-methylimidazole. Hence, the process is unsatisfactory in respect of saving of expensive solvents, good yield and simplicity and economy of operation. On the other hand, high conversion would be desirable because then the distillative removal of unconverted imidazoline would no longer be necessary. This advantage would be particularly important when preparing highmelting imidazoles, for example 1,2-diphenylimidazole.

German Laid-Open Application Nos. DOS 2,729,017, DOS 2,728,976 and DOS 2,733,466 describe processes for the preparation of imidazoles by converting 2-imidazolines at from 300° to 600° C. in the presence of zinc oxide or of a mixture of zinc oxide and aluminum oxide as the catalyst.

According to German Pat. No. 1,231,249, imidazole can be prepared by converting N,N'-diformylethylenediamine in the gas phase over a zinc oxide catalyst, at from 250° to 800° C. In this process, the yield of imidazole is from 42% to 80% of theory. All the Examples show that additionally nitrogen is introduced as an entraining agent or diluent, at a concentration of from 1 to 999 moles of nitrogen per mole of starting material. According to the data in the patent, the yields are unsatisfactory if zinc oxide is used as the sole catalyst. As shown in the description (column 2, lines 29 to 36) the catalysts are prepared in a simple manner and have no special structural characteristics except for a particle size of 0.2–0.4 mm. In contrast to the process disclosed in U.S. Pat. No. 2,847,417, where the description states the yield to be very low, no hydrogen is used; in all the Examples, nitrogen is employed, in an amount of from 45 to 60 moles per mole of starting material. The best yield of imidazole, namely 80% (Example 2) is obtained with a catalyst containing 78 percent by weight of zinc oxide, 7 percent by weight of aluminum oxide, 5 percent by weight of calcium oxide, 5 percent by weight of potassium sulfate, 2 percent by weight of magnesium oxide, 1 percent by weight of chromium-III oxide, and 2 percent by weight in all of iron-III oxide, sodium oxide and potassium oxide at 500° C. in the presence of nitrogen.

In contrast to the process of German Pat. No. 1,231,249, the later German Laid-Open Application DOS No. 2,729,017 does not employ N,N'-diformyl-1,2-diamines; instead, 1,2-diamines are reacted with formic acid over zinc oxide or over zinc oxide and aluminum oxide, preferably having a specific structure, at from 300° to 600° C. It is stated explicitly that when using this catalyst an addition of hydrogen is neither advantageous nor necessary, since the formation of tarry polymers or deposits on the catalyst, and a rapid regression of catalyst activity, are not observed. A comparison of the method of preparation of imidazole (Example 2) with the best procedure in German Pat. No. 1,231,249 (Example 2) shows that the zinc oxide/aluminum oxide catalyst of special structure gives a substantially poorer yield (69.2%), even in the presence of nitrogen and at 550° C., than does the catalyst, consisting of 9 components and zinc oxide of any desired structure, described in Example 2 of German Pat. No. 1,231,249.

French Pat. No. 1,266,702 describes the reaction of a mixture of an alkylenediamine and formaldehyde, advantageously at 315°–431° C., over a supported noble metal catalyst. In all the Examples, a platinum catalyst on aluminum oxide is used. The yields are unsatisfactory. It is stated that though supported cobalt molybdate can be used as the catalyst, it does not necessarily give equally good results (cf. page 2, last paragraph). The patent explains that only the genuine compound cobalt molybdate, and not a mixture of cobalt oxide and molybdenum oxide, can be used. Aluminum oxide is stated to be the carrier.

We have found that imidazoles of the formula

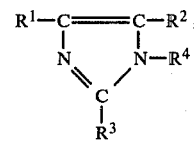

where $R^1$, $R^2$, $R^3$ and $R^4$ may be identical or different and each is an aliphatic, cycloaliphatic, araliphatic or aromatic radical or hydrogen, are obtained in an advantageous manner by reacting imidazolines in the presence of a metal catalyst at an elevated temperature, if a 2-imidazoline of the formula

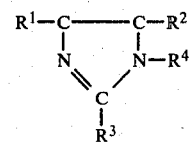

where $R^1$, $R^2$, $R^3$ and $R^4$ have the above meanings, is reacted at from 250° to 500° C. in the presence of (a)

molybdenum oxide and (b) nickel oxide and/or cobalt oxide and (c) aluminum oxide, silicon dioxide and/or silicates as the catalysts.

Further, we have found that, in an advantageous embodiment of the process, in a first step an N,N'-diformyl-1,2-diamine of the formula

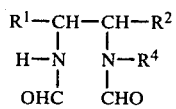

where $R^1$, $R^2$ and $R^4$ have the above meanings, is reacted in the gas phase at from 200° to 400° C. in the presence of zinc oxide and/or aluminum oxide as the catalyst, and, in a second step, the reaction mixture obtained, containing a 2-imidazoline II, is reacted at from 250° to 500° C. in the presence of (a) molybdenum oxide and (b) nickel oxide and/or cobalt oxide and (c) aluminum oxide, silicon dioxide and/or silicates as the catalysts.

Where 1,2-diphenylimidazoline is used, the reaction can be represented by the following equation:

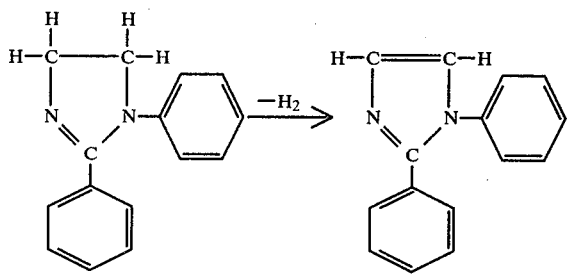

Compared to the conventional processes, the process according to the invention gives imidazoles more simply and more economically, in good yield and high purity. The use of sulfur compounds as reactants is avoided, and nevertheless surprisingly high yields are achieved. The reaction does not have to be carried out under reduced pressure. Advantageously, it is carried out in the gas phase so that 2-imidazolines which are unstable in the liquid phase can be further reacted without prior isolation. Even if no additional hydrogen is introduced, formation of tarry polymers, deposits on the catalyst, caking of the catalyst and rapid regression of catalyst activity are not observed. Even after 2,000 hours' operation, the catalyst is in a free-flowing state. The long operating time increases the space-time yield. The length of possible operation between successive regenerations does not decrease progressively. The throughputs achievable, advantageously 100–300 g of starting material II/liter of catalyst per hour, also remain virtually unchanged after regeneration. Addition of hydrogen is neither necessary nor advantageous. Compared to the catalysts employed in the conventional processes, the novel catalysts are cheaper and easier to regenerate, and do not suffer significant poisoning over a lengthy period of operation. The overall result in respect of conversion and yield is better than in the prior art, especially on an industrial scale. All these advantageous aspects are surprising in view of the prior art.

Preferred starting materials II and accordingly preferred end products I are those where $R^1$, $R^2$, $R^3$ and $R^4$ may be identical or different and each is alkyl of 1 to 18 carbon atoms, especially of 1 to 8 carbon atoms, alkenyl which in particular contains one double bond, but may also contain a plurality of double bonds, and is of 2 to 18, preferably of 3 to 18, especially of 4 to 8, carbon atoms, cycloalkyl of 5 to 7 carbon atoms, aralkyl or alkylaryl of 7 to 12 carbon atoms, phenyl or hydrogen. The above radicals may additionally be substituted by groups which are inert under the reaction conditions, for example alkyl or alkoxy, each of 1 to 4 carbon atoms.

Examples of suitable starting materials II are 1-phenyl-2-imidazoline which is unsubstituted or is monosubstituted in the 2-position, 4-position or 5-position, or is disubstituted by identical or different substituents in two of these positions or trisubstituted by identical or different substituents in all three of these positions, these substituents being chosen from methyl, ethyl, allyl, crotyl, propyl, isopropyl, butyl, isobutyl, pentyl, sec.-butyl, tert.-butyl, hexyl, heptyl, octyl, oleyl, n-undec-11-en-1-yl, nonyl, decyl, octadecyl, benzyl, cyclohexyl, cyclopentyl, toluyl, xylyl, naphthyl, methoxyphenyl, ethoxyphenyl, ethylphenyl, dimethoxyphenyl and phenyl; homologous 2-imidazolines substituted in the 1-position by methyl, ethyl, allyl, crotyl, propyl, isopropyl, butyl, isobutyl, pentyl, sec.-butyl, tert.-butyl, hexyl, heptyl, octyl, oleyl, n-undec-11-en-1-yl, nonyl, decyl, octadecyl, cyclohexyl, cyclopentyl, benzyl, toluyl, xylyl, naphthyl, methoxyphenyl, ethoxyphenyl, ethylphenyl or dimethoxyphenyl; unsubstituted imidazoline, and imidazolines which are unsubstituted in the 1-position but are substituted in the 2-, 4- and/or 5-position in the manner stated above.

The reaction is carried out at from 250° to 500° C., advantageously from 280° to 480° C., preferably from 320° to 410° C., under atmospheric or superatmospheric pressure, continuously or batchwise. As a rule, the reaction mixture also serves as the solvent, but it is also possible to use organic solvents which are inert under the reaction conditions and advantageously do not form an azeotrope with water, for example aliphatic hydrocarbons, eg. petroleum ether or naphtha. Amongst the organic solvents, those of boiling point above 120° C., advantageously above 140° C., for example appropriate gasoline fractions boiling at 120°–160° C., are preferred.

The catalyst always contains 3 components, namely (a) molybdenum oxide, (b) nickel oxide, cobalt oxide or a mixture of both and (c) aluminum oxide, silicon dioxide or a silicate, or a mixture of 2 or more of these. The molar ratio of nickel oxide and/or cobalt oxide to molybdenum oxide is advantageously from 0.5 to 5, preferably from 1 to 2.6. The molar ratio of aluminum oxide, silicon dioxide and/or silicate to molybdenum oxide is advantageously from 5 to 50, preferably from 8 to 12. The molar ratio of molybdenum oxide to starting material II is advantageously from 0.1 to 1.5, preferably from 0.2 to 0.6.

The catalyst can furthermore, if desired, contain oxygen compounds of zinc, magnesium, chromium or phosphorus, preferably zinc oxide, magnesium oxide, chromium-III oxide, sodium chromate, sodium bichromate, chromium trioxide, phosphoric acid, phosphorus pentoxide, sodium phosphate or potassium phosphate, advantageously in a ratio of 0.6–20, preferably 4–10, percent by weight of such oxygen compounds, based on total weight of unsupported catalyst, or of 0.5–15, preferably 3–7, percent by weight of the oxygen compounds, based on total weight of supported catalyst. The catalyst may also contain potassium sulfate or sodium sulfate, advantageously in an amount of 0.1 to 1 percent by weight, based on total weight of unsupported catalyst, or 0.08–0.8 percent by weight, based on total weight of supported catalyst.

Instead of cobalt oxide, nickel oxide and molybdenum oxide, compounds of the 3 metals which form oxides under the reaction conditions may be used. Examples of suitable compounds of the metals are the hydroxides, the carbonates, bicarbonates, sulfates, nitrates, chlorides, bromides, acetates and formates.

Suitable forms of aluminum oxide are, for example, $\alpha$- and $\gamma$-aluminum oxide. If zinc oxide is used as an additional component, as mentioned above, it may also be employed as a zinc compound which gives zinc oxide under the reaction conditions, for example an aluminum oxide impregnated with zinc chloride or zinc sulfate. Instead of aluminum oxide, materials, or mixtures of materials, which contain this oxide may be used, for example aluminum silicate, magnesium aluminum silicate hydrate, dimagnesium aluminum silicate hydrate, sodium aluminum silicate, calcium aluminum silicate, fuller's earth, clays, bleaching earths, eg. bentonite, bauxite, pumice, andalusite, kaolin, allophanes, zeolites, mullite, corundum, hydrargillite and boehmite. Silicon dioxide is advantageously used in the form of silicic acid compounds and silicates, such as montmorillonite, florida earth, quartz and asbestos, as well as precipitated silica, silica gel and kieselguhr.

The catalyst can be unsupported or can be applied to a carrier, advantageously in an amount of from 1 to 18 percent by weight, based on carrier. Advantageously, the above silicon compounds and aluminum compounds are used simultaneously as a catalyst component, in the form of the $SiO_2$ and/or $Al_2O_3$ which they contain, and as a carrier for the oxides constituting components (a) and (b). However, it is also possible to use other carriers, such as titanium dioxide, zirconium dioxide, tin dioxide, active charcoal, alkaline earth metal sulfates and alkaline earth metal phosphates, eg. the calcium salts or barium salts, or appropriate mixtures of the above carriers. Preferred carriers are aluminum oxide, magnesium oxide and silicates.

The supported catalysts are prepared by conventional processes, for example by applying the nickel compound and/or cobalt compound, and the molybdenum compound, with or without the silicon compound and/or the aluminum compound, to the carrier, and drying and calcining the product, for example at from 400° to 1,200° C. in a reducing, oxidizing or inert atmosphere. It is also possible to impregnate the carrier, for example aluminum oxide, in its desired geometrical form, with a solution of one of the above compounds alone, or a combined solution of the nickel compound and/or cobalt compound and the molybdenum compound, for example an aqueous solution of nickel sulfate and molybdenum sulfate, and then to dry the product. Equally, the carrier, in the form of component (c), can be kneaded with the nickel compound and/or cobalt compound, with or without the molybdenum compound, and with water, after which the mixture is brought to the desired shape, dried and calcined at from 400° to 1,200° C.

The particle size of the supported or unsupported catalyst is preferably from 0.05 to 7, especially from 2 to 4 millimeters. The catalyst can be of any desired shape, for example in the form of pills, cylinders, extrudates, beads or granules. Preferably, a supported catalyst has a pore volume of 0.05–1 milliliter per gram, a specific surface area of from 1 to 300 square meters per gram and a bulk density of from 0.4 to 2.1 grams per milliliter.

Preferably, the unsupported or supported catalysts are employed in chip or bead form in a fluidized bed, for which it is advantageous to employ catalyst particles having sizes of from 0.005 to 3 mm, especially from 0.1 to 1 mm, preferably from 0.2 to 0.4 mm. The height of the fluidized catalyst bed is advantageously from 30 to 2,000, especially from 60 to 80, millimeters, or is advantageously selected to give a residence time of the starting material II, in the catalyst bed, of from 0.01 to 20, preferably from 5 to 10, seconds. Regarding the preparation of the catalysts, reference may be made to Houben-Weyl, Methoden der Organischen Chemie, Volume 4/2, pages 142 et seq. and Ullmanns Encyklopädie der technischen Chemie, Volume 9, pages 271 et seq.

The reaction is advantageously carried out in the presence of an inert gas. Preferred gases which are inert under the reaction conditions are noble gases, eg. xenon, argon, neon and helium; alkanes, eg. methane, ethane, propane, 2,2-dimethylpropane, butane, pentane and isobutane, and, more especially, nitrogen, carbon monoxide and/or carbon dioxide, and corresponding mixtures, in particular including $CO/H_2$ mixtures. Per mole of starting material II, it is advantageous to use from 5 to 100 moles of inert gas, especially from 20 to 80 moles of nitrogen, or $CO/H_2$ mixtures in amounts corresponding to from 1 to 100, advantageously from 2 to 50, especially from 3 to 18, moles of carbon monoxide and from 1 to 100, advantageously from 3 to 50, and especially from 6 to 20, moles of hydrogen. In the case of gas mixtures, moles of inert gas refers to the average molar content of the mixture. The mixture can also contain other gaseous or vaporous components. Preferably, the exit gas from the reaction according to the invention is recycled entirely or partially, and used as a $CO/H_2$ gas mixture. An advantageous composition of the recycle gas is from 30 to 90, especially from 50 to 75, percent by weight of CO, from 3 to 15, especially from 5 to 7, percent by weight of hydrogen and additionally, in general, from 0 to 50, especially from 10 to 40, percent by weight of $CO_2$, from 0 to 30, especially from 0 to 10, percent by weight of nitrogen, from 0 to 10, especially from 0.5 to 5, percent by weight of ammonia, from 0 to 15, especially from 0.5 to 10, percent by weight of the diamine from which the starting material II is derived, and from 0 to 12, especially from 0.1 to 6, percent by weight of methane.

The reaction can be carried out as follows: the solid, liquefied or, advantageously, vaporous starting material II, mixed with inert gas, advantageously in the form of nitrogen or of the reaction exit gas, used as recycle gas, is passed, at the reaction temperature, over a fixed bed of the catalyst or supported catalyst. The vaporous reaction mixture issuing from the reactor is dedusted, if necessary, in a cyclone, and condensed in a cooled receiver. The end product is then advantageously isolated by fractional distillation. However, it can also be isolated by recrystallization or by reprecipitation from suitable solvents, for example by means of toluene, dimethylformamide or dilute acids, for example formic acid. The residence time in the fixed bed is advantageously from 0.2 to 20 seconds.

In a preferred embodiment of the process, the starting material II is reacted in a fluidized bed, at the reaction temperature. The catalyst or supported catalyst can be fluidized by means of the starting mixture or of the inert gas alone, advantageously in the form of nitrogen or of the above recycle gas, being employed as a fluidization gas under atmospheric, reduced or superatmospheric pressure. Accordingly, the total amount, or only a proportion, of the starting material II can be introduced into the fluidized bed reactor separately from the fluidization gas. Advantageously, the starting material II is kept in the liquid state in a heated stock vessel and is metered into a vaporizer upstream of the fluidized bed reactor. Advantageously, a slight stream of inert gas, advantageously from 5,000 to 50,000 parts by volume/hour, of nitrogen or of the above recycle gas is passed through the vaporizer at the same time. The vaporized starting material is passed through the catalyst bed together with the stream of cycle gas. However, it is also possible to feed the starting material II, in a solid form, advantageously with particle sizes of from 0.1 to 3 millimeters, or in a liquid form, directly into the fluidized bed reactor, either separately from the inert gas or together with the latter. The process according to the invention can be carried out in a simple or sub-divided, open or closed fluidized bed system, with or without recirculation of the fluidization dust. Reference may be made to Ullmanns Encyklopädie der technischen Chemie, Volume 1, pages 916–933, in respect of the reactors, method, process variants and reaction conditions. The reaction mixture is worked up in the manner described above. The residence time in the fluidized bed is advantageously from 0.2 to 20 seconds.

In an advantageous embodiment, the vaporous reaction mixture is passed, after reaction, into a separating column, the end product is taken off at the bottom and the remaining mixture is passed, from the top of the column, into a receiver where the condensable constituents, essentially water and the diamine from which the starting material II is derived, are condensed. A proportion of the off-gas, advantageously a proportion which contains the amounts of CO and $H_2$ mentioned above, is passed into a washing column, then dried, and employed as recycle gas.

In a preferred embodiment, the reaction is carried out in a fluidized bed and at the same time a proportion of the catalyst, advantageously from 0.33 to 10, preferably from 2 to 5, percent by weight, based on the total amount of catalyst in the fluidized bed, is withdrawn per hour, under atmospheric or superatmospheric pressure, batchwise or continuously, and a corresponding amount of regenerated catalyst introduced. The duration of operation of the fluidized bed may be the duration of a single continuous operation, or the duration of operation of several batchwise reactions with the same catalyst. In continuous operation, especially in a fluidized bed reactor, a ratio of from 0.1 to 3, preferably from 0.2 to 1.7, moles of nickel oxide and/or cobalt oxide, from 0.1 to 1.5, preferably from 0.2 to 0.6, mole of molybdenum oxide, and from 1 to 30, preferably from 1.6 to 7.2, moles of component (c) per hour per mole of starting material II is employed as a rule. The catalyst can be introduced, and withdrawn, by means of conventional equipment for conveying solids, for example conveying pumps or conveying screws.

The withdrawn catalyst can be regenerated either continuously, advantageously by being cycled from the point of withdrawal via the regeneration operation back to the fluidized bed, or can be regenerated batchwise. Advantageously, the regeneration or reactivation of the catalyst is also carried out in a fluidized bed reactor. In the latter, the height of the bed is advantageously from 30 to 2,000 millimeters and the residence time of the catalyst from 10 to 300, preferably from 3 to 50, hours. The fluidizing gas employed in the regeneration reactor, ie. the regenerating gas, can be the inert gas, gas mixture and recycle gas referred to earlier, where necessary with addition of steam and air or oxygen. The regeneration is as a rule carried out at from 300° to 600° C., preferably from 400° to 500° C., under atmospheric or superatmospheric pressure, advantageously using from 20,000 to 500, preferably from 2,000 to 600, grams of inert gas or gas mixture per hour per kilogram of catalyst, and with air or oxygen, preferably in an amount of, or equivalent to, from 100 to 10, especially from 70 to 20, moles of oxygen per mole of component (a). If necessary, the catalyst can, after withdrawal from the regenerator, be freed from catalyst dust, for example by means of a cyclone or electrostatic filter in the form of a tubular filter, and additional catalyst can be fed to the reaction according to the invention, in order to compensate for catalyst losses. Advantageously, this embodiment allows continuous operation, without having to stop in order to regenerate the catalyst. Catalyst dust formed can be separated off in a simple manner in the regeneration without causing a reduction in catalyst activity or in yield.

In a preferred embodiment, the process is carried out in two steps and an N,N'-diformyl-1,2-diamine is used as the starting material III. Preferred starting materials III are those where $R^1$, $R^2$ and $R^4$ have the preferred meanings of the radicals $R^1$, $R^2$ and $R^4$ in the starting materials II. Where N,N'-diformyl-1,2-diaminopropane is used, the reaction can be represented by the following equation:

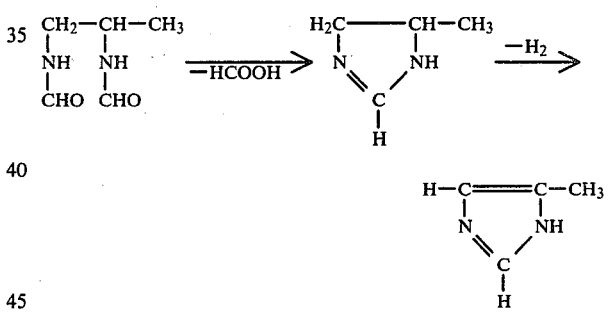

Compared to the conventional processes, the process according to the invention gives 2-imidazoles, starting from easily accessible diamines, more simply and more economically, in good yield and high purity. A further advantage of the process is that the reaction mixture which contains the imidazoline formed in the first step does not detract from the activity of the catalyst (components (a), (b) and (c)) used in the second step.

Examples of suitable starting materials III are the N,N'-diformyl compounds of ethylenediamine, 1,2-propylenediamine, 1,2-butylenediamine, 1,2-pentylenediamine, 1,2-n-hexylenediamine, 1,2-n-heptylenediamine, 1,2-n-octylenediamine, 1,2-n-nonylenediamine, 1,2-n-decylenediamine, 1,2-n-octadecylenediamine, 2,3-butylenediamine, 2,3-pentylenediamine, 2,3-hexylenediamine, 2,3-heptylenediamine, 2,3-octylenediamine, 2,3-nonylenediamine, 2,3-decylenediamine, 3,4-hexylenediamine, 3,4-heptylenediamine, 3,4-octylenediamine, 3,4-nonylenediamine, 3,4-decylenediamine, 4,5-octylenediamine, 4,5-nonylenediamine, 4,5-decylenediamine and 5,6-decylenediamine; ethylenediamines monosubstituted in the 1-position, or substituted in both the 1- and the 2-position, by benzyl and/or phenyl; ethylenediamines substituted by the above alkyl groups in the 1-position and by benzyl or phenyl in the 2-position; and the N-methyl-, N-ethyl-, N-propyl-, N-isopropyl-, N-butyl-, N-isobutyl-, N-sec.-butyl-, N-tert.-butyl-, N-benzyl- and N-phenyl-derivatives of the above N,N'-diformyl-1,2-diamines.

The reaction is as a rule carried out continuously, at from 200° to 390° C., advantageously from 210° to 370° C., under atmospheric or superatmospheric pressure, as a rule under a pressure of not less than 1 bar, advantageously from 1 to 5 bar, preferably from 1.2 to 2.5 bar. As a rule, the reaction mixture also serves as the solvent, but where appropriate the above organic solvents which are inert under the reaction conditions and preferably do not form an azeotrope with water may be used.

The catalyst used is zinc oxide or aluminum oxide or a mixture of these, advantageously in a gram-atom ratio of zinc to aluminum of from 1 to 50, preferably from 8 to 10, and employing from 0.1 to 1, preferably from 0.2 to 0.4, gram atom of zinc per mole of starting material II. Examples of aluminum oxide and of zinc compounds which give zinc oxide under the reaction conditions are the above aluminum and zinc compounds and silicon compounds containing aluminum and zinc. The catalyst may be unsupported or may be supported on a carrier, advantageously using from 1 to 18 percent by weight of catalyst, based on carrier. Equally, the above aluminum compounds may, in the form of the $Al_2O_3$ which they contain, serve both as a catalyst component and as a carrier for the zinc oxide. Advantageous carriers are those mentioned above. Regarding the preparation of the supported catalysts and of the catalyst particles, reference may be made to the conditions described above for the 3-component catalyst (a+b+c). The conditions and procedures described above for the second step also preferably apply to the first step, in particular in respect of the fluidized bed, particle size, height of the catalyst bed, residence time, amount of inert gas, use of nitrogen or recycle gas and composition of the recycle gas.

If desired, other oxides, for example iron-III oxide, may be used as auxiliary catalysts additionally to the zinc oxide; advantageously, from 0.2 to 2.0, especially from 0.8 to 1.8, moles of Fe-III oxide are used per mole of zinc oxide. An advantageous combination is that of zinc oxide and iron-III oxide on a silicon dioxide carrier, for example silica or silica gel, advantageously using from 12 to 20 percent by weight of $Fe_2O_3$, based on $SiO_2$, and from 150 to 250 percent by weight of $Fe_2O_3$, based on ZnO.

The two-step reaction can be carried out as follows: the vaporous starting material III, mixed with inert gas, is passed, at the reaction temperature of the first step, over the catalyst or supported catalyst in a first tubular reactor or fluidized bed reactor. It is advantageous to employ a residence time of from 1 to 40, especially from 3 to 20, seconds in the reaction space in the case of the first step. The mixture leaving the reactor is then, in the second step, reacted in the manner described above over the 3-component catalyst (a+b+c), and the end product is isolated as described above. The conditions mentioned, for example in respect of flow of inert gas and fluidized bed procedure for the second step, can also be used in the first step. The residence time in the first step is advantageously from 0.01 to 20 seconds in the case of a fluidized bed or from 3 to 20 seconds in a fixed bed. Using the above procedures, it is also possible to carry out both steps in a fixed bed or, advantageously, the 1st step in a fluidized bed and the 2nd step in a fixed bed.

The imidazoles I obtainable by the process of the invention are valuable starting materials for the preparation of dyes, crop protection agents, textile auxiliaries, catalysts for polyurethanes and epoxy resins, surfactants and drugs, for example the corresponding nitroimidazoles. Imidazoles I are also used as catalysts for polymerization reactions and aldol condensations. Regarding their use, reference may be made to the above publications and to Ullmanns Encyklopädie der technischen Chemie (3rd edition), Volume 8, page 499 and (4th edition), Volume 13, pages 173–175.

In the Examples which follow, parts are by weight and bear the same relation to parts by volume as that of the kilogram to the liter.

EXAMPLE 1

75 parts per hour of fused 1-phenylimidazoline are metered per hour from a heated metering vessel into a horizontal quartz vaporizer heated to 300° C. The vapors, together with 5,000 parts by volume of $N_2$ per hour, are passed through a fluidized bed reactor heated to 400° C. The reactor is an electrically heated quartz tube which is located vertically on the vaporizer and which at the bottom terminates in a fused-in quartz frit. The quartz tube is half-filled with 260 parts of a catalyst comprising 3 percent by weight of nickel oxide, 15 percent by weight of molybdenum oxide, 77 percent by weight of γ-aluminum oxide and 5 percent by weight of $P_2O_5$ (particle size 0.1–0.3 mm). The residence time in the catalyst zone, when the latter is fluidized, is 1.5 seconds. The height of the catalyst zone, when the latter is fluidized, is 8 mm. The vapors leaving the reactor are condensed and subjected to fractional distillation. 69 parts per hour (95.8% of theory, based on converted starting material II) of 1-phenylimidazole, of boiling point 110°–112° C./2 mbar are obtained in addition to 2 parts of unconverted 1-phenylimidazoline, of melting point 45° C. The conversion is 97.3 percent, based on starting material II employed. The yield remains the same even after 2,000 hours' operation.

EXAMPLE 2

100 parts of 1,2-diphenylimidazoline and 50,000 parts by volume of nitrogen are passed, per hour, through a fluidized bed reactor heated to 380° C. Using a procedure similar to Example 1, 60.3 parts per hour (67.6% of theory, based on converted starting material II) of 1,2-diphenylimidazole, of melting point 90° C., are obtained; the conversion is 90 percent, based on starting material II employed. The yield remains the same even after 2,000 hours' operation.

EXAMPLE 3

100 parts of 1-phenyl-2-p-tolyl-imidazoline and 50,000 parts by volume of nitrogen are passed, per hour, through a fluidized bed reactor heated to 350° C. Using a procedure similar to Example 1, 70.7 parts per hour (78.2% of theory, based on converted starting material II) of 1-phenyl-2-p-tolyl-imidazole, of melting point 119° C., are obtained. The conversion is 91.2%, based on starting material II employed. The yield remains the same even after 2,000 hours' operation.

EXAMPLE 4

100 parts of 1-phenyl-2-(3',4'-dimethylphenyl-)imidazoline and 50,000 parts by volume of nitrogen are passed, per hour, through a fluidized bed reactor heated to 400° C. Using a procedure similar to Example 1, 62.2 parts per hour (70.2% of theory, based on converted starting material II) of 1-phenyl-2-(3',4'-dimethylphenyl)-imidazole of melting point 146°–147° C. (after recrystallization from ethyl alcohol) are obtained. The conversion is 89.3 percent, based on starting material II employed. The yield remains the same even after 2,000 hours' operation.

EXAMPLE 5

100 parts of 1-phenyl-2-cyclohexylimidazoline and 50,000 parts by volume of nitrogen are passed, per hour, through a fluidized bed reactor heated to 350° C. The material leaving the reactor is fractionated through a column and, at a boiling point of 118° C./0.1 mm Hg, 74.4 parts of 1-phenyl-2-cyclohexylimidazole, corresponding to a yield of 84.1% of theory, based on converted starting material II, are obtained. The conversion is 89.3 percent, based on starting material II employed. The yield remains the same even after 2,000 hours' operation.

EXAMPLES 6 TO 10

The imidazoles I listed in Table 1 are obtained by a method similar to that of Example 1.

cipitated (melting point 65°–67° C.) is filtered off and dried.

(b) 90 parts per hour of N,N'-diformyldiaminopropane, from a stock vessel, and 600,000 parts of nitrogen per hour are passed through a fluidized bed reactor heated to 360° C. The reactor consists of a vertical, electrically heated quartz tube terminating, at the bottom, in a quartz frit. The fluidized bed reactor is followed by an externally heated fixed bed reactor, in which the second reaction stage takes place. The residence time is 1.7 seconds in the first stage and 6 seconds in the second stage. The reaction temperatures are 330° C. (1st stage) and 360° C. (2nd stage), the height of the fluidized bed is 80 millimeters and the height of the catalyst in the fixed bed is 600 millimeters. The 1st stage employs 300 parts of a catalyst consisting of 90 percent by weight of zinc oxide and 10 percent by weight of aluminum oxide (pore volume 0.5 milliliter per gram; specific surface area 250 square meters per gram; bulk density 1.1 gram per milliliter; particle size 0.1–0.3 millimeter). The 2nd stage employs 910 parts of a catalyst consisting of 3.1 percent by weight of nickel oxide, 17.5 percent by weight of molybdenum trioxide, 5.8 percent by weight of $P_2O_5$ and 73.6 percent by weight of γ-aluminum oxide, in the form of extrudates of 1.5 millimeters diameter. The vapors leaving the reactor are condensed and subjected to fractional distillation. 46 parts per hour (81% of theory, based on starting material II employed) of 4-methylimidazole, of melting point 45° C., are obtained. The conversion is 95.3 percent.

| Example | Parts | Starting material II | Temperature, °C. | Parts of catalyst | Composition in % by weight | End product | Melting point (°C.) | Yield, % of theory |
|---|---|---|---|---|---|---|---|---|
| 6 | 100 | 4,5-dihydroimidazoline | 350 | 250 | 0.5 $Na_2O$ | imidazole | 90 | 82.1 |
| 7 | 100 | 2-methyl-4,5-dihydroimidazoline | 370 | 280 | 3 NiO | 2-methyl-imidazole | 145 | 89.3 |
| 8 | 100 | 2-phenyl-4,5-dihydroimidazoline | 340 | 350 | 5 $P_2O_5$ | 2-phenyl-imidazole | 145 | 88.2 |
| 9 | 100 | 4-methyl-4,5-dihydroimidazoline | 380 | 280 | 15 $MoO_3$ | 4-methyl-imidazole | 45 | 84.7 |
| 10 | 100 | 2-ethyl-4-methyl-4,5-dihydroimidazoline | 340 | 300 | 76.5 γ-$Al_2O_3$ | 2-ethyl-4-methyl-imidazole | 38 | 83.5 |

EXAMPLE 11

(a) 180 parts of 1,2-diaminopropane are mixed with 320 parts of methyl formate at 25°–30° C., whilst stirring and cooling. When the reaction mixture has cooled to 0° C., the N,N'-diformyldiaminopropane which has pre- The yield remains the same even after 2,000 hours' operation.

EXAMPLES 12 TO 16

The reactions of which the details are given in Table 2 below are carried out similarly to Example 11.

TABLE 2

$$R^1—CH—CH—R^2$$
$$\begin{array}{cc} | & | \\ H-N & N-R^3 \\ | & | \\ OHC & CHO \end{array}$$

| Example | Starting material III parts/hour | Parts of $N_2$/hour | $R^1$ | $R^2$ | $R^3$ | Temperature in 1st stage (°C.) | Parts of catalyst in 1st stage | Composition in % by weight |
|---|---|---|---|---|---|---|---|---|
| 13 | 80 | 600,000 | H | H | H | 300 | 250 | |
| 14 | 90 | 600,000 | H | $CH_3$ | H | 250 | 250 | 10% of γ-aluminum oxide 90% of zinc oxide |
| 15 | 80 | 600,000 | H | H | H | 300 | 250 | |
| 16 | 80 | 600,000 | H | H | H | 300 | 250 | |

| Example | Temperature in 2nd stage (°C.) | Parts of catalyst in 2nd stage | Composition in % by weight | Yield of end product I, in % of theory | Melting point in °C. |
|---|---|---|---|---|---|
| 13 | 340 | 600 | 6 of NiO | 80.2 | 90 |
| 14 | 360 | 1,000 | 15 of $MoO_3$ | 78.3 | 45 |
| 15 | 335 | 620 | 79 of $MgSiO_3$ | 77.3 | 90 |

TABLE 2—Continued

| 16 | 340 | 600 | 5.1 of CoO<br>13.4 of MoO₃<br>81.5 of γ-aluminum oxide | 78.2 | 90 |
|---|---|---|---|---|---|

EXAMPLE 17

50 parts per hour of N,N'-diformyldiaminopropane are vaporized in a quartz vaporizer at 300° C. and the vapors, together with 310,000 parts by volume of recycle gas per hour, are passed through a fluidized bed reactor and subsequently through a fixed bed reactor. The recycle gas contains 73.4 percent by weight of CO, 6.55 percent by weight of $H_2$, 2.3 percent by weight of $NH_3$, 3.3 percent by weight of methane and 14.45 percent by weight of $CO_2$. The 1st stage (ie. the entry stage, employing the fluidized bed) contains 250 parts of catalyst and the 2nd stage (the fixed bed) contains 700 parts of catalyst. The residence times are 2.6 seconds in the 1st stage and 8 seconds in the 2nd stage. The reaction temperatures are 330° C. (1st stage) and 350° C. (2nd stage), the height of the fluidized bed is 80 millimeters and the height of the fixed bed is 1,000 millimeters. The catalyst contained in the reactor employed for the 1st stage consists of 80% of ZnO and 20% of γ-aluminum oxide (catalyst particle size 0.1–0.3 millimeter; pore volume 0.3 milliliter per gram; specific surface area 180 square meters per gram; bulk density 1 gram per milliliter). The reactor employed for the 2nd stage (ie. the fixed bed reactor) contains 700 parts of a catalyst in the form of extrudates of 1.5 millimeters diameter, consisting of 3.1 percent by weight of nickel oxide, 17.5 percent by weight of molybdenum trioxide, 5.8 percent by weight of $P_2O_5$ and 73.6 percent by weight of γ-aluminum oxide. After working up by a method similar to Example 1, 21.5 parts per hour ((82.3% of theory, based on starting material II employed) of imidazole of melting point 90° C. are obtained. The conversion is 96.5 percent, based on diamide employed. The yield remains the same even after 2,000 hours' operation. A proportion of the exit gases is returned, as the recycle gas referred to above, to the fluidized bed reactor.

We claim:

1. In a process for the preparation of imidazoles of the formula

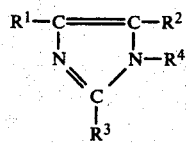

where $R^1$, $R^2$, $R^3$ and $R^4$ may be identical or different and ech is an aliphatic, cycloaliphatic araliphatic or aromatic radical or hydrogen, by reacting imidazolines in the presence of a metal catalyst at elevated temperature, the improvement which comprises reacting a 2-imidazoline of the formula

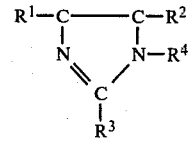

where $R^1$, $R^2$, $R^3$ and $R^4$ have the above meanings, at from 250° to 500° C. in the presence of a catalyst mixture containing at least three components and consisting essentially of (a) molybdenum oxide and (b) nickel oxide and/or cobalt oxide and (c) aluminum oxide and/or silicon dioxide and/or silicates.

2. A process as claimed in claim 1, wherein, in a first step, an N,N'-diformyl-1,2-diamine of the formula

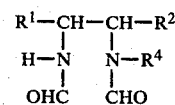

where $R^1$, $R^2$ and $R^4$ have the above meanings, is reacted in the gas phase, at from 200° to 400° C., in the presence of zinc oxide and/or aluminum oxide as the catalyst and the resulting reaction mixture, containing a 2-imidazoline II, is reacted, in a second step, at from 250° to 500° C., in the presence of said catalyst mixture.

3. A process as claimed in claim 1, wherein the reaction is carried out at from 280° to 480° C.

4. A process as claimed in claim 1, wherein the reaction is carried out using from 0.5 to 5 moles of nickel oxide and/or cobalt oxide per mole of molybdenum oxide in said catalyst mixture.

5. A process as claimed in claim 1, wherein the reaction is carried out with from 5 to 50 moles of aluminum oxide and/or silicon oxide and/or silicate per mole of molybdenum oxide in said catalyst mixture.

6. A process as claimed in claim 1, wherein the reaction is carried out with from 0.1 to 1.5 moles of molybdenum oxide per mole of starting material II.

7. A process as claimed in claim 1, wherein the reaction is carried out with from 1 to 18 percent by weight of said catalyst mixture, based on carrier.

8. A process as claimed in claim 1, wherein the reaction is carried out with a supported or unsupported catalyst having a particle size of from 0.05 to 7 millimeters.

9. A process as claimed in claim 1, wherein the reaction is carried out with a supported catalyst having a pore volume of from 0.05 to 1 milliliter per gram, a specific surface area of from 1 to 300 square meters per gram and a bulk density of from 0.4 to 2.1 grams per milliliter.

10. A process as claimed in claim 1, wherein the reaction is carried out in a fluidized bed of an unsupported or supported catalyst in the form of chips or beads.

11. A process as claimed in claim 1, wherein the reaction is carried out in the presence of an inert gas.

12. A process as claimed in claim 1, wherein the reaction is carried out in a fluidized bed reactor from which a proportion of the catalyst is withdrawn and into which a corresponding amount of regenerated catalyst is introduced.

* * * * *

UNITED STATES PATENT AND TRADEMARK OFFICE
CERTIFICATE OF CORRECTION

PATENT NO. : 4,340,744

DATED : July 20, 1982

INVENTOR(S) : Helmut Schwarz, Toni Dockner, Uwe Kempe, Herbert Krug, Werner Praetorius, Peter Magnussen, Ewald Gallei, and Erich Fehr It is certified that error appears in the above-identified patent and that said Letters Patent are hereby corrected as shown below:

Claim 1, line 4 (excluding the structural formula):

change "ech" to --each--.

Signed and Sealed this

Twenty-first Day of September 1982

[SEAL]

Attest:

Attesting Officer

GERALD J. MOSSINGHOFF

Commissioner of Patents and Trademarks